(12) United States Patent
Shams Es-haghi et al.

(10) Patent No.: US 11,389,402 B2
(45) Date of Patent: Jul. 19, 2022

(54) DEVICES AND METHODS FOR DELIVERING PHARMACEUTICAL DRUGS TO PATIENTS

(71) Applicant: Purdue Research Foundation, West Lafayette, IN (US)

(72) Inventors: Siamak Shams Es-haghi, West Lafayette, IN (US); Gustavo A. Guzman Cardozo, Lafayette, IN (US); Mukerrem Cakmak, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/009,734

(22) Filed: Jun. 15, 2018

(65) Prior Publication Data

US 2019/0060231 A1    Feb. 28, 2019

Related U.S. Application Data

(60) Provisional application No. 62/520,177, filed on Jun. 15, 2017, provisional application No. 62/520,643, filed on Jun. 16, 2017.

(51) Int. Cl.
| | |
|---|---|
| *A61K 9/06* | (2006.01) |
| *A61K 31/4709* | (2006.01) |
| *A61K 47/32* | (2006.01) |
| *A61K 9/00* | (2006.01) |

(52) U.S. Cl.
CPC .............. *A61K 9/06* (2013.01); *A61K 9/0014* (2013.01); *A61K 31/4709* (2013.01); *A61K 47/32* (2013.01)

(58) Field of Classification Search
CPC ......... A61K 9/06; A61K 9/0014; A61K 47/32
See application file for complete search history.

(56) References Cited

U.S. PATENT DOCUMENTS

2012/0045651 A1*    2/2012   Myung ................... C08L 75/06
                                                              525/127

OTHER PUBLICATIONS

Lee, W-F. et al. "Studies on Preparation and Swelling Properties of the Isopropylacrylamide/Chitosan Semi-IPN and IPN Hydrogels" J. Appl. Polym. Sci. 2001, 82, 2487 (Year: 2001).*
Gitsov, I. et al. "Novel Functionality Grafted Pseudo-Semi-interpenetrating Networks Constructed by Reactive Linear-Dendritic Copolymers" JACS 2003, 125 (37), 11228-11234 (Year: 2003).*
Es-Haghi, S.S. et al. "On the Necking Phenomenon in Pseudo-Semi-Interpenetrating Double-Network Hydrogels" Macromolecules 2013, 46, 6203-6208 (Year: 2013).*
Es-Haghi, S.S. et al. "Fabrication of Tough Hydrogels from Chemically Cross-Linked Multiple Neutral Networks" Macromolecules 2016, 49, 8980-8987 (Year: 2013).*
S. Shams Es-Haghi and R.A. Weiss; "Fabrication of Tough Hydrogels from Chemically Cross-Linked Multiple Neutral Networks"; ACS Publications; 2016 American Chemical Society; 49; 8980-8987.

* cited by examiner

*Primary Examiner* — Andrew S Rosenthal
(74) *Attorney, Agent, or Firm* — Hartman Global IP Law; Gary M. Hartman; Domenica N. S. Hartman

(57) ABSTRACT

Methods and devices suitable for delivering a pharmaceutical drug to patient. Such a device includes a multiple-network pseudo-interpenetrating polymer network (pseudo-IPN) hydrogel containing the drug. The hydrogel comprises loosely cross-linked polymeric networks that interpenetrate and are grafted to each other.

17 Claims, 5 Drawing Sheets
(4 of 5 Drawing Sheet(s) Filed in Color)

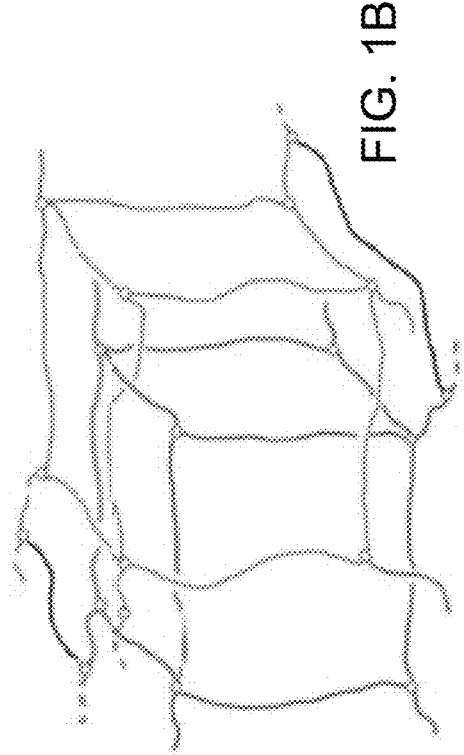
FIG. 1A
FIG. 1B
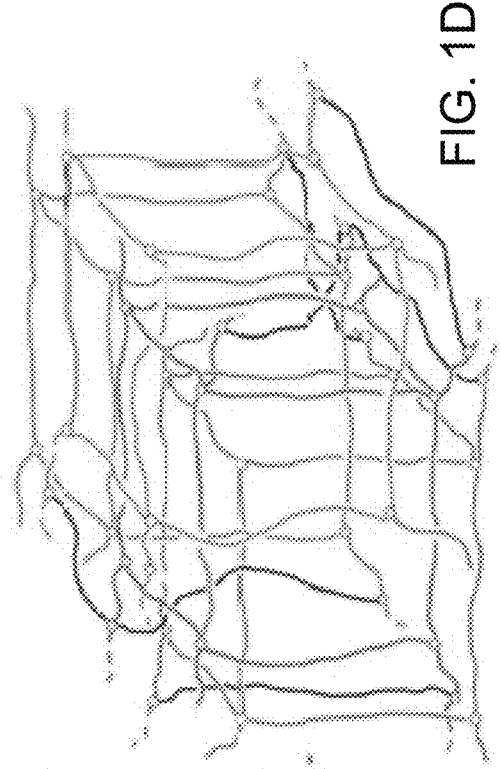
FIG. 1C
FIG. 1D

DEVICES AND METHODS FOR DELIVERING PHARMACEUTICAL DRUGS TO PATIENTS

CROSS REFERENCE TO RELATED APPLICATIONS

This application claims the benefit of U.S. Provisional Application Nos. 62/520,177 filed Jun. 15, 2017, and 62/520,643 filed Jun. 16, 2017, the contents of which are incorporated herein by reference.

BACKGROUND OF THE INVENTION

The present invention generally relates to medical technologies. The invention particularly relates to technologies for delivering pharmaceutical drugs (therapeutics) to patients.

For many years, controlled drug release research has been focused on achieving zero-order, continuous release of medication, with some significant success. However, an on-demand (dosage-, spatial-, and temporal-controllable drug release) control of drug delivery is desired in many clinical situations, as it promises to improve therapeutic efficacy and lessen side effects. As a result, researchers have heavily pursued spatial- and/or temporal-controlled drug release from biomaterials in recent years. Within the large spectrum of biomaterials capable of extended drug release, "smart" stimuli-responsive hydrogels have been postulated as ideal candidates, as they are able to respond to changes in the environment by altering their structure. To date, a significant number of different stimuli have been used for triggering drug release in biomaterials (mostly hydrogels), including pH, temperature, light, electric fields, and magnetic fields. Nevertheless, the clinic translation of methods based on these stimuli is often thwarted by the difficulty of a precise trigger control in a physiological environment.

Compared to other stimuli, mechanically activated release remains promising. First, on-demand mechanical force can be generated during normal daily motions, including tension and compression in muscles, cartilage and bones, as well as shear stress in blood vessels. Second, patient-controlled drug release through movement might increase patient compliance. Lastly, application of mechanical force provides a reliable trigger for drug release in both magnitude and direction. Even though most of the common patient motions comprise extension rather than compression, the majority of experimental systems presented thus far are believed to involve hydrogels in which compression triggers the drug release. The apparent reason for the scarcity of extension-triggered systems is the limited strain tolerance of most hydrogels. In wearable applications, strains can be as large as 50%, which exceeds the strain capacity of most hydrogel systems. A series of new devices attempted to solve this issue by embedding hydrogel micro- or nano-capsules in strain-resistant elastomeric substrates, and relied on enlarged surface area for diffusion and Poisson's ratio-induced compression due to deformation to promote drug release. Although this approach is promising, fabrication procedures are complicated and the hydrogel loses some of the intrinsic benefits of being a "soft" material, like the low interfacial tension at the gel-aqueous solution interface (which affects biocompatibility) and the low modulus. At the same time, it becomes difficult to regulate the released dosage in a repeatable manner, due in part to the structural changes that may occur in the material during cyclic deformation. A fundamental study on the dynamic relationship between the cyclic deformation characteristics of the hydrogels themselves and the relevant release profile under strain is yet to be presented.

Another issue relating to controlled drug release research concerns the tendency for drug-containing media, including hydrogels of the types noted above, to exhibit an initial high burst of drug release that may be detrimental to the health or therapeutic treatment of a patient.

In view of the above, it can be appreciated that there are certain shortcomings or disadvantages associated with technologies for delivering pharmaceutical drugs to patients, and that it would be desirable if improved technologies and methodologies were available for such purposes.

BRIEF DESCRIPTION OF THE INVENTION

The present invention provides technologies, methods, and devices suitable for delivering pharmaceutical drugs to patients.

According to one aspect of the invention, a device for delivering a water-soluble drug to a patient includes a multiple-network pseudo-interpenetrating polymer network (pseudo-IPN) hydrogel containing the drug. The hydrogel comprises loosely cross-linked polymeric networks that interpenetrate and are grafted to each other.

Other aspects of the invention include methods of using devices of the type described above. Particular but nonlimiting examples include configuring a device to be applied to the skin of a patient for mechanically-activating the release of a drug.

Technical aspects of technologies, methods, and devices as described above preferably include the ability of a multiple-network pseudo-IPN hydrogel to deliver drugs in response to straining of the hydrogel, and/or reducing if not avoiding an initial high burst of drug release that may be detrimental to the health or therapeutic treatment of a patient.

Other aspects and advantages of this invention will be further appreciated from the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A, 1B, 1C, and 1D schematically represent depict, respectively, SN, DN, TN, and QN multiple-network pseudo-IPN hydrogels as nonlimiting examples of loosely cross-linked pseudo-interpenetrating polymer networks capable of use with the present invention. Dark (black) chains seen in FIGS. 1B, 1C, and 1D represent that, in addition to the networks interpenetrating each other, there are grafted links between the networks.

DETAILED DESCRIPTION OF THE INVENTION

Figure 2:
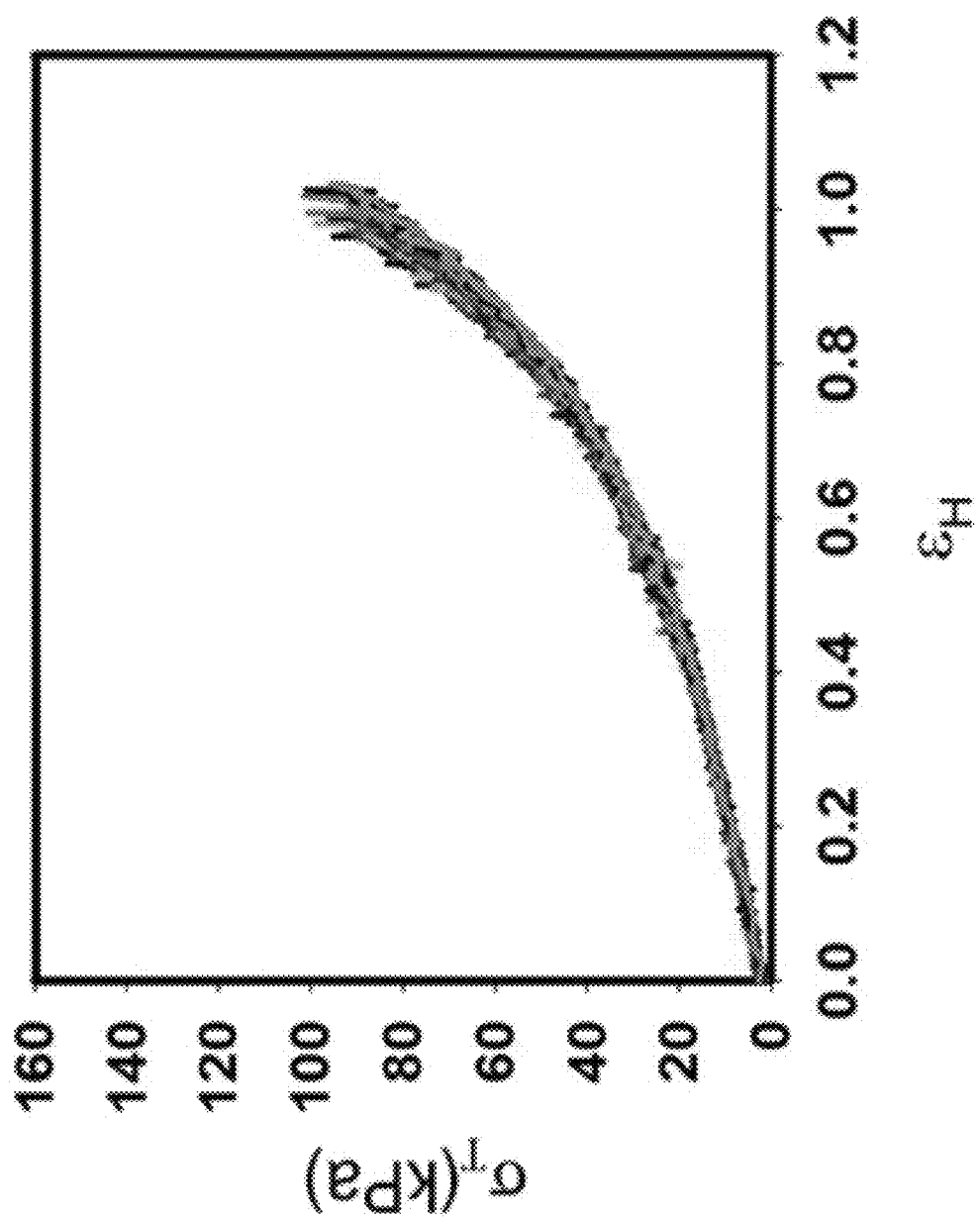
FIG. 2 is a graph showing cyclic tensile loading of a DN hydrogel synthesized from acrylamide, as a nonlimiting example of a particular multiple-network pseudo-IPN hydrogel capable of use with the present invention.

The term "patient" will be used herein to refer to an intended recipient of a pharmaceutical drug, and such a recipient may be a human, animal, or other entity that a drug is intended to be delivered to. The term "initial burst release" will be used herein to refer to the level of a drug initially released by a carrier that contains and delivers the drug. The terms "multiple-network pseudo-interpenetrating polymer network hydrogel" and "multiple-network pseudo-IPN hydrogel" will be used herein to refer to a hydrogel that comprises two or more polymer networks (e.g., double-network (DN), triple-network (TN), quadruple-network (QN), etc.) that interpenetrate or semi-interpenetrate each other and are grafted to each other so as to be at least partially bonded to each other.

Methods and devices described herein utilize multiple-network pseudo-IPN hydrogels that contain loosely cross-linked polymeric networks that interpenetrate and are grafted to each other so that the hydrogels are mechanically tough, are preferably capable of being stretched to large deformations without any molecular level damage, and preferably exhibit complete strain recovery upon release of stress used to induce a large deformation. The hydrogels are predominantly made up of water (for example, greater than 70% by weight), and therefore are particularly well suited as a delivery medium for water-soluble drugs, whereby such drugs can be dissolved in a device formed of or containing such a hydrogel and then released therefrom, preferably in a controlled fashion.

Shams Es-haghi et al., "Fabrication of Tough Hydrogels from Chemically Cross-Linked Multiple Neutral Networks," Macromolecules 2016, 49, 8980-8987, incorporated herein by reference, discloses a method that was developed to fabricate multiple-network pseudo-IPN hydrogels from neutral polymer networks, for example, water-soluble monomers. Shams Es-haghi et al. demonstrated that multiple-network hydrogels made from loosely cross-linked pseudo-interpenetrating network (IPN) hydrogels are capable of achieving large deformations under simple uniaxial extension and compression. Multiple-network pseudo-IPN hydrogels with single-network (SN) and double-network (DN) structures exhibited a behavior similar to an extensible soft tissue, and no strain localization or mechanical damage was observed after performing loading-unloading-reloading tensile experiments. The present invention is based in part on the similarity of stress/strain behavior of DN hydrogels reported in Shams Es-haghi et al. to that of an extensible biological tissue like skin, and observations that their loading-unloading mechanical behavior resulted in no mechanical damage. In particular, investigations leading to the present invention evaluated whether multiple-network pseudo-IPN hydrogels of the type produced by Shams Es-haghi et al. may be candidates for drug release under deformation. More particularly, investigations leading to the present invention evaluated the mechanical responses and molecular orientations of multiple-network hydrogels to cyclic uniaxial extension, the effect of network number on drug release profiles, and the effect of uniaxial deformation on drug release rates of DN hydrogels.

According to a preferred but nonlimiting aspect of the invention, the investigations leading to the present invention demonstrated the feasibility of strain-induced drug delivery with multiple-network pseudo-IPN hydrogels. Multiple-network pseudo-IPN hydrogels described herein are mechanically tough and biocompatible, and unlike other hydrogels exhibit very high elasticity and low hysteresis (i.e., they undergo little or no molecular level degradation from large deformation). As such, the multiple-network pseudo-IPN hydrogels are comfortable when applied to a patient's skin and can be easily adapted to on-skin application at joints, for example, an elbow, knee, finger joint, etc., of a patient. Furthermore, the investigations leading to the present invention demonstrated that drug delivery devices utilizing these hydrogels exhibit drug release rates that can be tuned by the level of deformation applied to the hydrogel. In particular, higher drug release rates can be achieved by increasing deformation.

According to another preferred but nonlimiting aspect of the invention, the investigations leading to the present invention determined that increased numbers of networks in multiple-network pseudo-IPN hydrogels had the unexpected beneficial effect of suppressing initial burst releases of drugs from a device utilizing such a hydrogel as a deliver medium. An initial burst release is typically observed in conventional hydrogels (as well as other drugs and drug application modes such as eye drops) and is often unwanted for drug therapies since a high local release of a drug may lead to undesirable effects including unusually high early concentrations of a drug at the applied area, which in some cases may reach toxic levels depending on the drug in question. By suppressing an initial burst release, a more uniform or consistent distributed delivery of a drug may be achieved that can prolong the efficacy of the drug.

As discussed above, multiple-network pseudo-IPN hydrogels can be synthesized from neutral water-soluble monomers. The building blocks of multiple-network pseudo-IPN hydrogels are loosely cross-linked polymeric networks that interpenetrate and are grafted to each other. The prefix "pseudo" is used herein to refer to grafting between the networks. In effect, the hydrogels are synthesized by sequential free radical polymerization of loosely cross-linked polymeric networks. Single-network (SN), double-network (DN), and triple-network (TN) hydrogels can be used as precursors for synthesizing DN, TN, and quadruple-network (QN) multiple-network pseudo-IPN hydrogels. FIGS. 1A, 1B, 1C, and 1D schematically represent, respectively, SN, DN, TN, and QN pseudo-IPN hydrogels. Further details of the synthesis and molecular structures of these tough chemically cross-linked hydrogels can be found in Shams Es-haghi et al.

Previous research reported in the aforementioned paper to Shams Es-haghi et al. has shown that multiple network pseudo IPN hydrogels can be synthesized from acrylamide to exhibit intriguing mechanical behaviors. According to Shams Es-haghi et al., single network (SN) hydrogels were highly extensible, but were not found to be able to sustain high loads. Double network (DN) hydrogels exhibited stress-strain behavior similar to that of extensible biological tissues, for example, human skin. Moreover, the DN hydrogels were able to undergo large tensile deformations without being mechanically damaged, such that the DN hydrogels were able to completely recover to their original shape upon removal of stress. In other words, no hysteresis was observed in loading-unloading tensile tests.

Investigations leading to the present invention evidenced that multiple-network pseudo-IPN hydrogels are capable of being used to control drug release rate and substantially reduce the initial burst release of a drug contained by the hydrogel. In one investigation, synthesis of multiple-network hydrogels was carried out using procedures consistent with the aforementioned paper to Shams Es-haghi et al. Acrylamide (AAm) and N,N'-methylenebis(acrylamide) (MBAA) were purchased from Sigma-Aldrich and used as received. A photoinitiator, 2-oxoglutaric acid (OXGA), was obtained from Fluka Chemical Co. and used as received. Moxifloxacin hydrochloride was obtained in its commercial eyedrop form, Vigamox®. Briefly, a single-network (SN) hydrogel was synthesized from a reaction mixture that was prepared by adding initiator (0.1 mol % with respect to AAm) and crosslinker (0.01 mol % with respect to AAm) to a 4 M solution of AAm in deionized (DI) water. The SN hydrogel was made by exposing the reaction mixture for 20 minutes to 365 nm ultraviolet (UV) light (15 mW/cm2) after injecting it into a glass mold made of two parallel glass slides. After producing the SN hydrogel, it was immersed into the same reaction mixture until an equilibrium swelling was achieved. The swollen SN gel was then placed between two parallel glass slides and exposed for 20 minutes to 365 nm UV light (15 mW/cm2) to make a double-network (DN) hydrogel. The same procedure was used to make other multiple-network hydrogels. In effect, SN, DN, triple-network (TN) and quadruple-network (QN) hydrogels were used as precursors to produce DN, TN, QN, and pentuple-network (PN) hydrogels, respectively. In this study, the number of networks was increased to five (PN hydrogel). Hydrogels were kept in DI water after synthesis and the water was replaced with fresh water at least five times to remove unreacted monomers.

Drug release from undeformed multiple-network hydrogels was evaluated with 2×2 cm samples of the synthesized hydrogels, and strain-triggered drug delivery from the synthesized hydrogels was evaluated with 5×2 cm samples. All samples underwent submersion in 5 mL of a moxifloxacin hydrochloride solution (50 µg/mL) in PBS (1×) for 48 hours at 37° C. Subsequently, the samples were transferred to fresh PBS (×1) solution (5 mL). The 5×2 cm samples were clamped in a holding apparatus at a fixed stretching ratio prior to being transferred to the fresh PBS solution. The holding apparatus maintained the deformation of the strain-triggered hydrogel samples at selected fixed stretch ratios while submerged in the release medium, which was sampled and replenished to investigate drug release profiles while keeping samples deformed. The cumulative release under stretching was normalized by the release in the absence of deformation.

In each case, the PBS solution was extracted and replaced with fresh PBS solution each hour to maintain infinite sink conditions. Samples were kept in a G24 Environmental Incubator Shaker from New Brunswick Scientific, mixed at 100 rpm and at 37° C. The samples were analyzed by UV-VIS spectrometry. Moxifloxacin hydrochloride concentration was determined by following the absorbance of peaks at 204 and 289 nm and comparing with calibration curves.

FIG. 2 is a graph plotting the true stress-strain behavior of one of the DN hydrogels in cyclic tensile loading during ten cycles, and evidences that loading and unloading deformation paths coincided indicating that no discernible damage occurred in the molecular structure of the hydrogel. This property was considered to be remarkable for a chemically cross-linked hydrogel. By increasing the number of networks, the hydrogels were found to become tougher. For example, a thin ribbon of QN hydrogel containing more than 80 wt % water was shown to be able to sustain 4 kgf.

Figure 3:
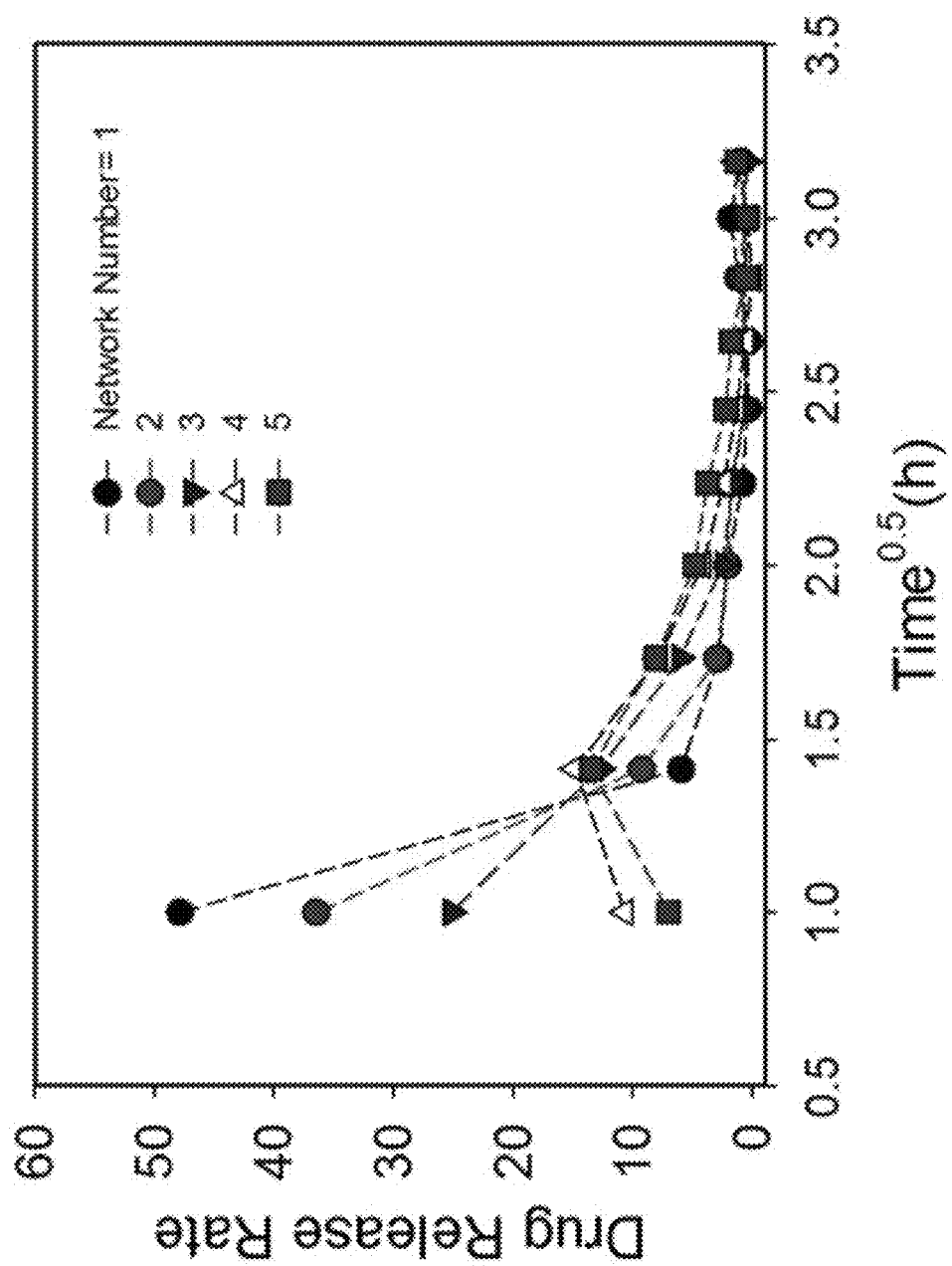
FIG. 3 is a graph showing a drug release profile that indicates the effect that the number of networks of a multiple-network pseudo-IPN hydrogel had on the drug release rate therefrom.

Increasing the number of networks was shown to slow drug release rates and suppress the burst of drug release during initial deformation of the hydrogel and subsequently enable increased rates. FIG. 3 is a graph indicating the release profiles for DN, TN, QN, and PN hydrogels. Increasing early "burst" suppression was demonstrated as the number of networks increased from one to five, with networks exceeding three networks (QN, and PN hydrogels with, respectively, four and five networks) particularly exhibiting suppressed initial burst releases. These hydrogels with high network numbers also exhibited high subsequent release rates.

Figure 4:
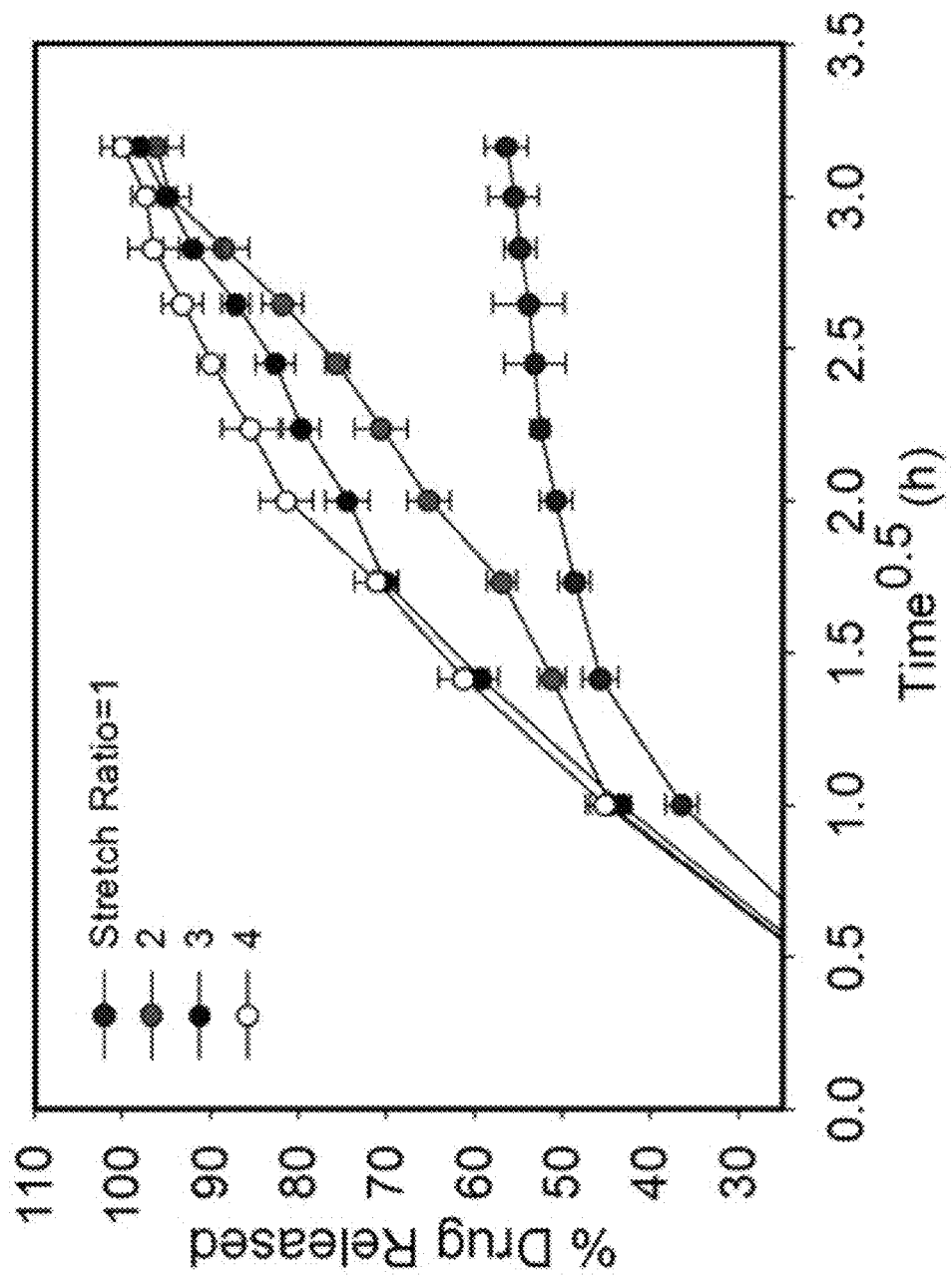
FIG. 4 is a graph showing a drug release profile that indicates the effect that stretching (strain) of a double-network pseudo-IPN hydrogel had on the drug release rate therefrom.

FIG. 4 is a graph that evidences that strain-induced drug release from a double-network pseudo-IPN hydrogel under tension was capable of achieving controlled drug release rates. During stretching, the polymer network became conformationally distorted, and there was an increase in free volume and surface area. The increase in free volume increases diffusion rates while the increase in surface area increases the area of contact in between the release media and the hydrogel. Mechanical signaling did not significantly affect the initial "burst" release, with about 45% of the drug being released at a stretch ratio of 4 for the deformed sample compared to about 38% for the undeformed sample (stretch ratio of 1). By normalizing the release in stretched samples by the release in the absence of deformation, it was seen that at high extension ratios the amount of drug released in a ten-hour period could be up to about 1.8 times greater than that for an undeformed sample.

The investigations reported above evidenced that antibiotic release rates from multiple-network hydrogels, from a single-network (SN) to a pentuple-network (PN) hydrogel, was lower for hydrogels with higher numbers of networks, and that hydrogels with higher numbers of networks also exhibited significantly lower "bursts" of drug release. Therefore, it was concluded that the number of networks can be used as a design factor to control the drug release profile of a multiple-network hydrogel.

Figure 5:
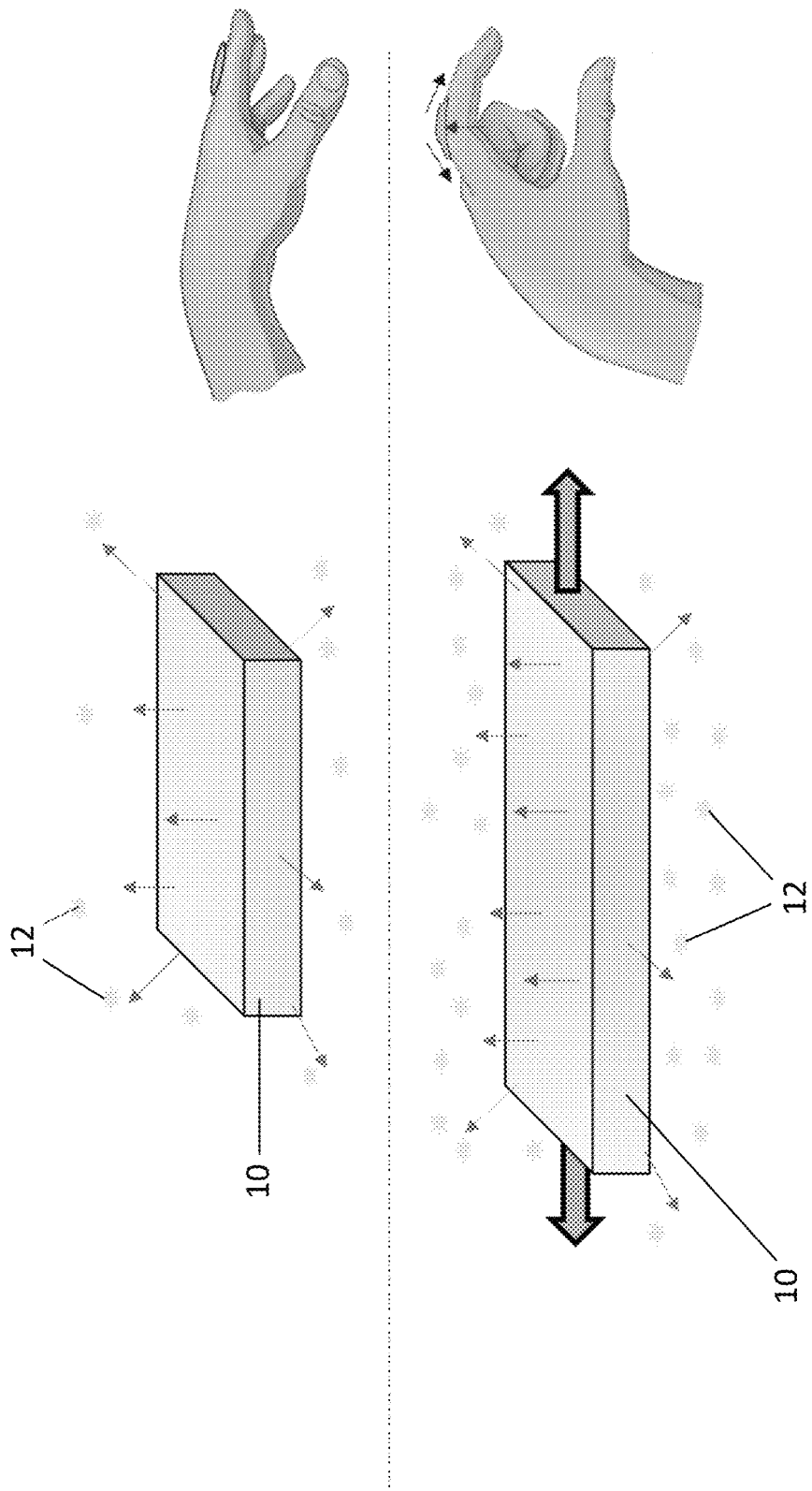
FIG. 5 schematically represents a nonlimiting example of strain-promoted drug delivery with a device that incorporates a double-network pseudo-IPN hydrogel of the present invention.

FIG. 5 schematically represents a device 10 formed of a DN hydrogel and processed to contain a drug. The device 10 is represented as applied to a human finger joint to utilize a desired and controlled release profile for the absorbed drug. As represented in the top image of FIG. 5, a relatively slow release of the drug 12 occurs when the device 10 is subject to little or no strain (stretching), and the bottom image represents that a much higher release rate occurs when the device 10 is at a higher level of strain, for example, up to about 300%. The release kinetics of such a device are transformed from Fickian (time dependent) to anomalous with increasing extensions. Advantageously, such a device can be activated by on-demand mechanical forces that can be generated during normal daily motions, including tension and compression in muscles, cartilage, and/or bones, as well as shear stress in blood vessels. Furthermore, such a device can enable patient-controlled drug release through movement, which may have the potential for increasing patient compliance, and allows the magnitude and direction of an applied mechanical force to provide a reliable trigger for drug release.

Multiple-network pseudo-IPN hydrogels of the types disclosed herein are believed to be particularly well suited for mechanically-activating the release of drugs in view of their unprecedented toughness and their ability to be stretched to strains exceeding the strain capacity of most hydrogel systems, in other words, in excess of 50% and often up to at least 700% of their original dimension, without molecular level degradation. Moreover, investigations leading to the present invention evidenced the ability of DN hydrogels to exhibit stress-strain behaviors that are similar to that of extensible biological tissues and undergo large cyclic deformations without mechanical damage and while exhibiting high fatigue resistance, indicating their ability to be an excellent candidate for drug release under tension and for mechanically-triggered drug release applications. For example, DN hydrogels could be used during daily motions of patients and for extended periods of time. Due to the high toughness of multiple-network hydrogels and durability of DN hydrogels in cyclic tensile loading, they do not need to be embedded in another medium as drug-loaded hydrogel particles. While the investigations reported above evidenced the suitability of multiple-network pseudo-IPN hydrogels for mechanically-activating the release of drugs, it is also within the scope of the invention that the hydrogels could be used to form a device or incorporated into a device that can be chemically-activated to release a drug.

While the invention has been described in terms of specific or particular embodiments and investigations, it should be apparent that alternatives could be adopted by one skilled in the art. For example, the device and its components could differ in appearance and construction from the embodiments described herein and shown in the drawings, functions of certain components of the device could be performed by components of different construction but capable of a similar (though not necessarily equivalent) function, process parameters could be modified, and appropriate materials could be substituted for those noted. For example, though investigations leading to the present invention assessed multiple-network pseudo-IPN hydrogels synthesized from acrylamide, multiple-network pseudo-IPN hydrogels synthesized from other water soluble monomers are also within the scope of the invention, including but not limited to N,N-dimethylacrylamide, (hydroxyethyl)methacrylate, and 2-hydroxyethyl methacrylate. As such, it should be understood that the above detailed description is intended to describe the particular embodiments represented in the drawings and certain but not necessarily all features and aspects thereof, and to identify certain but not necessarily all alternatives to the represented embodiments and described features and aspects. As a nonlimiting example, the invention encompasses additional or alternative embodiments in which one or more features or aspects of a particular embodiment could be eliminated or two or more features or aspects of different disclosed embodiments could be combined. Accordingly, it should be understood that the invention is not necessarily limited to any embodiment described herein or illustrated in the drawings, and the phraseology and terminology employed above are for the purpose of describing the illustrated embodiments and investigations and do not necessarily serve as limitations to the scope of the invention. Therefore, the scope of the invention is to be limited only by the following claims.

The invention claimed is:

1. A device for delivering a drug to a patient, the device comprising a multiple-network pseudo-interpenetrating polymer network (pseudo-IPN) hydrogel containing the drug, the hydrogel comprising loosely cross-linked polymeric networks, wherein the chemical compositions of the polymeric networks are the same, each of the polymeric networks is hydrophilic, the polymeric networks interpenetrate and are grafted to each other, and the device releases the drug in response to mechanical straining of the hydrogel.

2. The device according to claim 1, wherein the drug is a water-soluble drug.

3. The device according to claim 1, wherein the number of polymeric networks in the hydrogel is greater than three to suppress an initial burst release of the drug to the patient.

4. The device according to claim 3, wherein the number of polymeric networks in the hydrogel is four or five.

5. The device according to claim 1, wherein the hydrogel is able to be stretched to strains in excess of 50% of an original dimension thereof without molecular level degradation.

6. The device according to claim 1, wherein the hydrogel is able to be stretched to strains of up to at least 700% of an original dimension thereof without molecular level degradation.

7. The device according to claim 1, wherein the hydrogel is synthesized from neutral water-soluble monomers.

8. The device according to claim 1, wherein the hydrogel is synthesized from acrylamide, N,N-dimethylacrylamide, (hydroxyethyl)methacrylate, or 2-hydroxyethyl methacrylate.

9. The device according to claim 1, wherein the device is configured to be applied to the skin of the patient for mechanically-activating the release of a drug.

10. A method of using the device according to claim 9 to deliver the drug to the patient, the method comprising straining the hydrogel and then applying the device to the skin of the patient.

11. The method according to claim 10, wherein the hydrogel is selectively strained to control the rate of delivery of the drug to the patient.

12. The method according to claim 11, wherein the rate of delivery of the drug to the patient is increased by increasing the strain in the hydrogel.

13. The method according to claim 10, wherein an initial burst release of the drug to the patient is suppressed by increasing the number of polymeric networks in the hydrogel.

14. The method according to claim 13, wherein the number of polymeric networks in the hydrogel is greater than three.

15. The method according to claim 13, wherein the number of polymeric networks in the hydrogel is four or five.

16. A method of using the device according to claim 1 to deliver the drug to the patient, the method comprising straining the hydrogel and then applying the device to the skin of the patient.

17. A device for delivering a drug to a patient, the device comprising a multiple-network pseudo-interpenetrating polymer network (pseudo-IPN) hydrogel containing the drug, the hydrogel comprising loosely cross-linked polymeric networks, wherein the chemical compositions of the polymeric networks are the same, each of the polymeric networks is hydrophilic, the polymeric networks interpenetrate and are grafted to each other, the device releases the drug in response to mechanical straining of the hydrogel and releases the drug at a release rate that increases with increasing levels of deformation applied to the hydrogel.

* * * * *